United States Patent [19]

Miller

[11] 4,414,423

[45] Nov. 8, 1983

[54] MULTISTEP OLIGOMERIZATION PROCESS

[75] Inventor: Stephen J. Miller, San Francisco, Calif.

[73] Assignee: Chevron Research Company, San Francisco, Calif.

[21] Appl. No.: 305,679

[22] Filed: Sep. 25, 1981

[51] Int. Cl.³ ............................................... C07C 2/02
[52] U.S. Cl. ................................... 585/517; 585/530; 585/533
[58] Field of Search ............... 585/517, 530, 533, 510

[56] References Cited

U.S. PATENT DOCUMENTS

| | | | |
|---|---|---|---|
| 3,325,465 | 6/1967 | Jones et al. | 260/94.9 |
| 3,756,942 | 9/1973 | Cattanach | 208/137 |
| 3,827,968 | 8/1974 | Givens et al. | 208/49 |
| 3,960,978 | 6/1976 | Givens | 585/531 |
| 4,211,640 | 7/1980 | Garwood et al. | 208/255 |
| 4,227,992 | 10/1980 | Garwood et al. | 208/46 |
| 4,238,318 | 12/1980 | Kouwenhoven et al. | 208/137 |
| 4,239,930 | 12/1980 | Allphin et al. | 585/517 |
| 4,263,465 | 4/1981 | Sheng et al. | 585/517 |
| 4,289,607 | 9/1981 | Kokotailo | 585/533 |
| 4,324,940 | 4/1982 | Dessau | 585/466 |

*Primary Examiner*—Curtis R. Davis
*Attorney, Agent, or Firm*—D. A. Newell; S. R. La Paglia; W. L. Stumpf

[57] ABSTRACT

A multistep process for preparing high-boiling hydrocarbons from normally gaseous hydrocarbons is disclosed.

10 Claims, 2 Drawing Figures

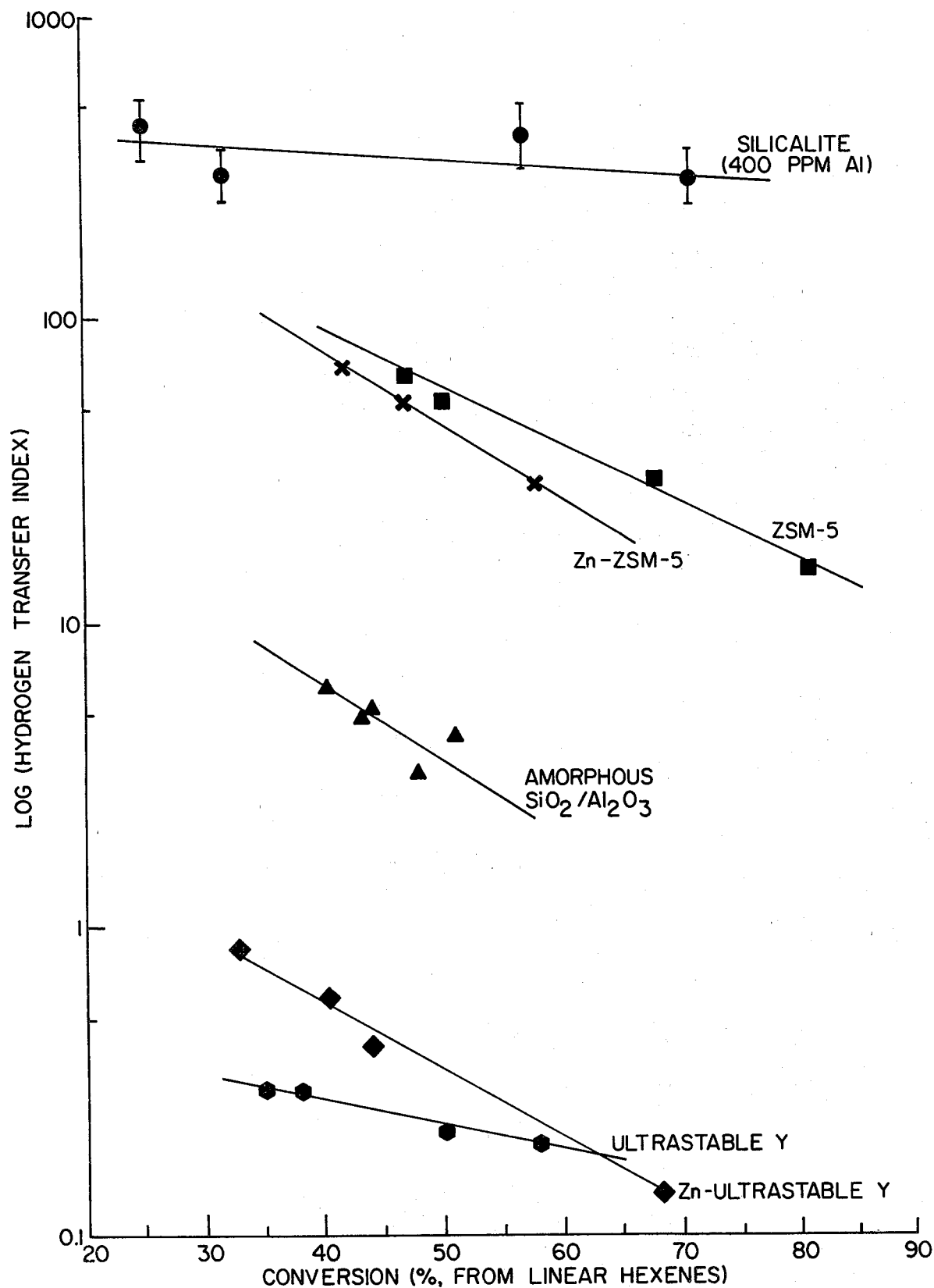
FIG._1.

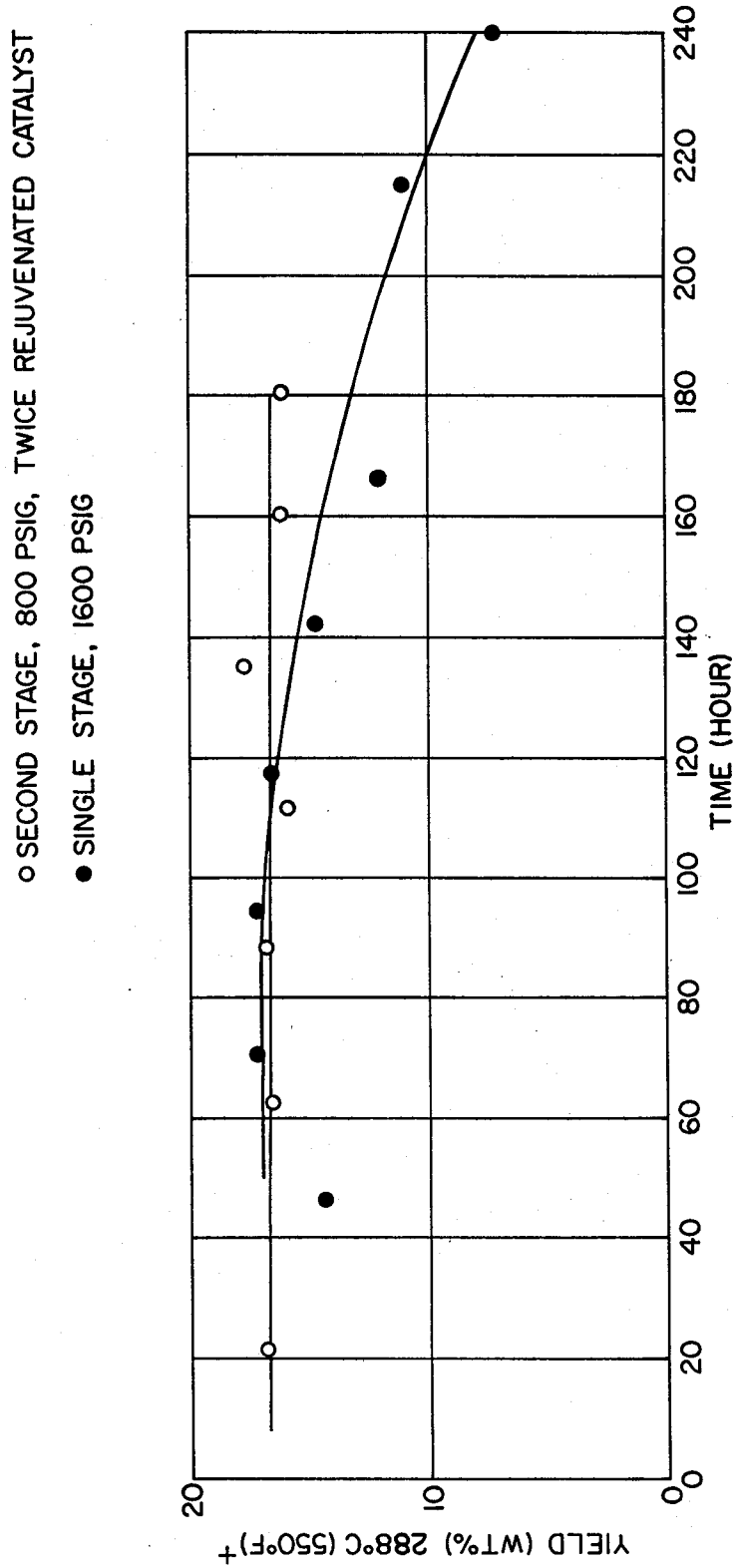

4,414,423

MULTISTEP OLIGOMERIZATION PROCESS

TECHNICAL BACKGROUND

During normal refinery operation, many processes produce large amounts of normally gaseous olefins. These compounds are useful as feeds for many processes, but often, because of the very large scale of the typical commercial plant, there is too large a quantity of olefins to be handled efficiently. As new processes such as low pressure nonhydrogenative ZSM-5 dewaxing as well as nonhydrogenative silicalite dewaxing come into use, the increasing supply of the normally gaseous olefins produced by catalytic cracking can be expected to increase even more dramatically. As the amount of gas produced increases, more and more equipment must be dedicated to gas handling. Since gas handling equipment, especially compressors, is bulky and expensive, it can be appreciated that there is a continuing search for efficient and cost-effective ways of increasing gas handling capabilities, especially for olefinic gases.

I have discovered a process which quickly, easily, and efficiently converts normally gaseous olefins to highly desirable mid-range and high boiling range products. The process dramatically reduces the necessity of having expensive gas handling equipment, yet uses convenient processing conditions and easily obtainable catalysts. Further, surprisingly long run lives can be obtained under the operating conditions of the process and reaction exotherms can be easily controlled.

TECHNICAL DISCLOSURE

My discoveries are embodied in a process for preparing high boiling hydrocarbons from normally gaseous olefins, comprising:

(a) contacting a feed comprising normally gaseous olefins with a first catalyst comprising an intermediate pore size silicaceous crystalline molecular sieve substantially free of hydrogen transfer activity, to produce a first effluent comprising normally liquid olefins; and (b) contacting at least part of the normally liquid olefins contained in said first effluent with a second catalyst comprising an intermediate pore size silicaceous crystalline molecular sieve substantially free of hydrogen transfer activity under oligomerization conditions to produce a second effluent wherein said second effluent comprises oligomers of said normally liquid olefins and wherein at least some of said oligomers are liquids under said oligomerization conditions.

The feeds to my process contain normally gaseous olefins. They typically contain paraffins also and are usually the products of standard refinery processes. FCC offgas, which contains large quantities of propenes and butenes, is a particularly good feed, as is the highly olefinic gaseous product of nonhydrogenative dewaxing processes.

The reaction conditions in the first reaction zone are such as to cause the normally gaseous olefins in the feed to oligomerize to form an effluent which contains normally liquid olefins, typically in the gasoline range. The first reaction zone can be operated at temperatures of 275° C. to about 475° C., pressures from subatmospheric to 65 bar, and hourly space velocities of 0.5 to 50. Of course in order to receive the benefits of my process, the operating pressure in the first zone is preferably the same as the reaction zone which is producing the feed. In the case where an FCC offgas is the feed, the typical operating pressure will be from about atmospheric to about 6 bar. Where nonhydrogenative ZSM-5 dewaxing is used, a pressure from about atmospheric to about 14 bar is preferred. Where nonhydrogenative silicalite dewaxing is used, the pressure can be above 14 bar.

The feeds to the second step of my process contain the normally liquid olefins produced by the first step. The second step is operated so that at least some of the oligomers produced in this second step are liquids under the conditions in that reaction zone. The most highly preferred operating conditions are such that at least some of both feed and product alkene components are liquids in the reaction zone.

Under standard operating procedures, it is normal both to know the chemical composition of feedstocks being introduced into a reaction zone and to set and control the temperature and pressure in the reaction zone. Once the chemical composition of a feed, or intermediate feed, is known, the temperatures and hydrocarbon partial pressures which will maintain all or part of the product as liquids can be determined using standard tables or routine calculations. Conversely, once the desired temperature and pressure to be used in the reaction zone are set, it becomes a matter of routine to determine what feeds and feed components would or would not be gases in the reactor and which oligomers would be liquids. These calculations involve using critical temperatures and pressures. Critical temperatures and pressures for pure organic compounds can be found in standard reference works such as CRC Handbook of Chemistry and Physics, International Critical Tables, Handbook of Tables for Applied Engineering Science, and Kudchaker, Alani, and Zwolinski, Chemical Reviews, 68, 659 (1968), all of which are incorporated herein by reference. The critical temperature for a pure compound is that temperature above which the compound cannot be liquefied regardless of pressure. The critical pressure, is the vapor pressure of the pure compound at its critical temperature. These points for several pure alkenes are listed below:

|  | $T_c$ °C. (°F.) | $P_c$-atm (bar) |
| --- | --- | --- |
| ethene | 9.21 (48.6) | 49.66 (50.3) |
| propene | 91.8 (197.2) | 45.6 (46.2) |
| 1-butene | 146.4 (295.5) | 39.7 (40.2) |
| 1-pentene | 191.59 (376.9) | 40 (40.5) |
| iso-2-pentene | 203 (397) | 36 (36.5) |
| 1-hexene | 230.83 (447.49) | 30.8 (31.2) |
| 1-heptene | 264.08 (507.34) | 27.8 (28.2) |
| 1-octene | 293.4 (560.1) | 25.6 (25.9) |
| 1-decene | 342 (648) | 22.4 (22.7) |

It can be appreciated that at temperatures above about 205° C. (401° F.), pure $C_5$ and normally gaseous lower olefins must be gaseous, while pure $C_6$ and higher olefins can still be liquefied by applying pressure. Similarly, above about 275° C. (527° F.) pure $C_8$ and higher olefins can be maintained in the liquid state, while pure $C_7$ and lower olefins must be gaseous.

Typical feeds are mixtures of compounds. But even so, once the chemical composition of the feed is known, the critical temperature and pressure of the mixture can be determined from the ratios of the chemicals and the critical points of the pure compounds. See for example, the methods of Kay and Edmister in Perry's Chemical Engineers Handbook, 4th Edition, pages 3-214, 3-215 (McGraw Hill, 1963), which is incorporated by reference.

The olefin chains can be branched. And, even though intermediate pore size molecular sieves are used, olefins having quaternary carbons (two branches on the same carbon atom) can be used. But where quaternary carbons are present, it is highly preferred that the branches are methyl. It appears that even though the intermediate pore size molecular sieves do not admit quaternary carbon atoms into their pore structures, they have the capability of causing one of the quaternary substituents to migrate to a different position on the olefin chain, thereby forming two tertiary sites and an entity which can enter the intermediate sized pores.

One of the surprising discoveries which my invention embodies is that under certain reaction conditions, $C_5$–$C_9$ normally liquid dimers and trimers of gaseous olefins can be oligomerized over intermediate pore size molecular sieves instead of being cracked to short chain compounds. Additionally, the oligomers produced are very highly desirable for use as mid- and high-range fuels.

The feed olefins can be prepared from any source by standard methods. Sources of such lower olefins can include FCC offgas, syngas (by use of CO reduction catalysts), low pressure, nonhydrogenative zeolite dewaxing, alkanols (using high silica zeolites), dewaxing with crystalling silica polymorphs, and thermal cracking offgas.

By "intermediate pore size silicaceous crystalline molecular sieve," as used herein, is meant two classes of silica containing crystalline materials. The first class includes material which, in addition to silica, contain significant amounts of alumina. These crystalline materials are usually called "zeolites," i.e., crystalline aluminosilicates. The second class of materials are essentially alumina-free silicates. These crystalline materials can include crystalline silica polymorphs, e.g., silicalite, chromia silicates, e.g., CZM, and ferrosilicates, e.g., U.S. Pat. No. 4,238,318.

All of these materials have the ability of sorting molecules based on the size or the shape, or both, of the molecules. The larger pore size materials will admit larger molecules than the smaller pore size materials. Intermediate pore size silicaceous crystalline molecular sieves have the unique characteristics of being able to differentiate between large molecules and molecules containing quaternary carbon atoms on the one hand, and smaller molecules on the other. Thus, the intermediate pore size materials have surprising catalytic selectivities by reason of their effective pore apertures, as well as highly desirable and surprising catalytic activity and stability when compared to larger pore size crystalline molecular sieves.

By "intermediate pore size," as used herein, is meant an effective pore aperture in the range of about 5 to 6.5 Angstroms when the molecular sieve is in the H-form. Molecular sieves having pore apertures in this range tend to have unique molecular sieving characteristics. Unlike small pore zeolites such as erionite and chabazite, they will allow hydrocarbons having some branching into the molecular sieve void spaces. Unlike larger pore zeolites such as the faujasites and mordenites, they can differentiate between n-alkanes and slightly branched alkanes on the one hand and larger branched alkanes having, for example, quaternary carbon atoms.

The effective pore size of the molecular sieves can be measured using standard adsorption techniques and hydrocarbonaceous compounds of known minimum kinetic diameters. See Breck, *Zeolite Molecular Sieves*, 1974 (especially Chapter 8) and Anderson et al, *J. Catalysis* 58, 114 (1979), both of which are incorporated by reference.

Intermediate pore size molecular sieves in the H-form will typically admit molecules having kinetic diameters of 5.0 to 6.5 Angstroms with little hindrance. Examples of such compounds (and their kinetic diameters in Angstroms) are: n-hexane (4.3), 3-methylpentane (5.5), benzene (5.85), and toluene (5.8). Compounds having kinetic diameters of about 6 to 6.5 Angstroms can be admitted into the pores, depending on the particular sieve, but do not penetrate as quickly and in some cases are effectively excluded. Compounds having kinetic diameters in the range of 6 to 6.5 Angstroms include: cyclohexane (6.0), 2,3-dimethylbutane (6.1), 2,2-dimethylbutane (6.2), m-xylene (6.1), and 1,2,3,4-tetramethylbenzene (6.4). Generally, compounds having kinetic diameters of greater than about 6.5 Angstroms do not penetrate the pore apertures and thus are not absorbed into the interior of the molecular sieve lattice. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms. Among the materials falling within this range are the zeolite ZSM-5, the crystalline silica polymorph silicalite, RE 29,948 organosilicates, and the chromia silicate, CZM.

In performing adsorption measurements to determine pore size, standard techniques are used. It is convenient to consider a particular molecule as excluded if it does not reach at least 95% of its equilibrium adsorption value on the zeolite in less than about 10 minutes (p/po=0.5; 25° C.).

Examples of intermediate pore size silicaceous crystalline molecular sieves include zeolites such as CZH-5 and members of the ZSM series, e.g., ZSM-5, ZSM-11, ZSM-12, ZSM-21, ZSM-23, ZSM-35, and ZSM-38. ZSM-5 is described in U.S. Pat. Nos. 3,702,886 and 3,770,614; ZSM-11 is described in U.S. Pat. No. 3,709,979; ZSM-12 is described in U.S. Pat. No. 3,832,449; ZSM-21 and ZSM-38 are described in U.S. Pat. No. 3,948,758; ZSM-23 is described in U.S. Pat. Nos. 4,076,842; ZSM-35 is described in U.S. Pat. No. 4,016,245; CZH-5 is disclosed in Ser. No. 166,863, Hickson, filed July 7, 1980. These patents and specifications are incorporated herein by reference. The intermediate pore size materials can include "crystalline admixtures" which are thought to be the result of faults occurring within the crystal or crystallite area during the synthesis of the zeolites. The "crystalline admixtures" are themselves zeolites but have characteristics in common, in a uniform or nonuniform manner, to what the literature reports as distinct zeolites. Examples of crystalline admixtures of ZSM-5 and ZSM-11 are disclosed and claimed in U.S. Pat. No. 4,129,424, Kokotailo, Oct. 21, 1980 (incorporated by reference). The crystalline admixtures are themselves intermediate pore size zeolites and are not to be confused with physical admixtures of zeolites in which distinct crystals or crystallites of different zeolites are physically present in the same catalyst composite or hydrothermal reaction mixture.

Other examples of intermediate pore size silicaceous crystalline molecular sieves include crystalline silica polymorphs which, as described before, are essentially alumina free.

"Essentially alumina free," as used herein, is meant the product silica polymorph (or essentially alumina-free silicaceous crystalline molecular sieve) has a silica:alumina mole ratio of greater than 200:1, preferably greater than 500:1, and more preferably greater than 1000:1. The term "essentially alumina free" is used because it is difficult to prepare completely aluminum free reaction mixtures for synthesizing these materials. Especially when commercial silica sources are used, aluminum is almost always present to a greater or lesser degree. The hydrothermal reaction mixtures from which the essentially alumina free crystalline silicaceous molecular sieves are prepared can also be referred to as being substantially aluminum free. By this usage is meant that no aluminum is intentionally added to the reaction mixture, e.g., as an alumina or aluminate reagent, and that to the extent aluminum is present, it occurs only as a contaminant in the reagents.

Intermediate pore size crystalline silicas include silicalite, disclosed in U.S. Pat. No. 4,061,724; the "RE 29,948 organosilicates" as disclosed in RE 29,948; and CZH-9 Ser. No. 264,767, Hickson, filed May 18, 1981. Intermediate pore size silicates, ferrosilicates and galliosilicates are disclosed in U.S. Pat. No. 4,238,318, Kouwenhoven et al, Dec. 9, 1980. Intermediate pore size chromia silicates, CZM, are disclosed in Ser. No. 160,618, Miller, filed June 28, 1980. All of these are incorporated by reference.

The most preferred molecular sieves are the zeolites ZSM-5, ZSM-11, and their crystalline admixtures, silicalite, RE 29,948 organosilicates, and CZM. Of course, these and other molecular sieves can be used in physical admixtures.

The silicaceous crystalline molecular sieves must be substantially free of hydrogen transfer activity. High hydrogen transfer activity is typically present in a catalyst as a result of a high aluminum content (low silica:alumina mole ratio) in a molecular sieve component. If the silica:alumina ratio is low, the catalyst will tend to convert the olefinic products and reactants to paraffins and aromatics rather than to oligomerize them, thereby greatly reducing or eliminating the benefits of the present invention. (Hydrogen transfer activity is to be distinguished from hydrogenation activity, which would saturate the alkenes to produce the corresponding alkanes.) The hydrogen transfer activity of the molecular sieve can be substantially lessened by using essentially alumina free silicaceous crystalline molecular sieves, and especially materials such as silicalite, the RE 29,948 organosilicates, and CZM.

Zeolitic silicaceous crystalline molecular sieve catalysts can be made substantially more active and stable for oligomerization by including the Group IIB metals, zinc or cadmium. A primary characteristic of these substituents is that they are weak bases, and are not easily reduced. These metals can be incorporated into the catalysts using standard impregnation, ion exchange, etc., techniques. Other metals such as calcium and the rare earths may be included in the catalyst. If hydrogen is not added to the feed, Group VIII metals (such as nickel, cobalt, palladium, and platinum) as well as other metals (such as vanadium, titanium, manganese, and rhenium) may also be included in the catalyst. Mixtures of these metals may also be present. Strongly basic metals such as the alkali metals are unsatisfactory as they poison substantially all of the polymerization sites on the zeolite. For this reason, the alkali metal content of the zeolite is less than 1%, preferably less than 0.1%, and most preferably less than 0.01%. The most preferred substituents for use are zinc and cadmium, of these zinc is preferred. Zinc and cadmium are present in the catalyst at from about 0.01 to about 10 wt. %.

The use of zinc or zinc compounds as the substituent on the zeolite molecular sieves, and even on the essentially alumina-free materials, gives surprising stability, yields, and activity in the liquid olefin oligomerization processes described herein.

The substantial absence of hydrogen transfer activity can be determined using standard laboratory procedures.

The polymerization processes of the present invention are surprisingly more efficient with small crystallite sieve particles than with larger crystallite particles. Preferably, the molecular sieve crystals or crystallites are less than about 10 microns, more preferably less than about 1 micron, and most preferably less than about 0.1 micron in the largest dimension. Methods for making molecular sieve crystals in different physical size ranges are known to the art.

The molecular sieves can be composited with inorganic matrix materials, or they can be used with an organic binder. It is preferred to use an inorganic matrix since the molecular sieves, because of their large internal pore volumes, tend to be fragile, and to be subject to physical collapse and attrition during normal loading and unloading of the reaction zones as well as during the oligomerization processes. Where an inorganic matrix is used, it is highly preferred that the matrix be substantially free of hydrocarbon conversion activity. It can be appreciated that if an inorganic matrix having hydrogen transfer activity is used, a significant portion of the oligomers which are produced by the molecular sieve may be converted to paraffins and aromatics and to a large degree the benefits of my invention will be lost.

The reaction conditions under which the oligomerization reactions of the second step take place include pressures sufficient to maintain at least some of the olefin oligomer product of the second step in the liquid state in the reaction zone. Of course, the larger the oligomer molecules, the lower the pressure required to maintain the liquid state at a given temperature. As described above, the operating pressure is intimately related to the chemical composition of the feed and the product, but can be readily determined. Generally, the required pressures range above about 30 bar and preferably above about 60 bar.

The second oligomerization reaction zone is typically operated below about 350° C., as above that temperature not only significant cracking of reactants and loss of oligomer product take place, but also significant hydrogen transfer reaction causing loss of olefinic oligomers to paraffins and aromatics takes place. Liquid hourly space velocities in the second zone can range from 0.05 to 20, preferably from 0.1 to about 4.

Once the effluent from the second oligomerization reaction zone is recovered, a number of further processing steps can be performed.

If it is desired to use the long chain compounds directly as fuels, the olefin oligomers can be hydrogenated.

All or part of the effluent of the second zone can be contacted with the molecular sieve catalyst in further reaction zones to further react unreacted alkenes and alkene oligomers with themselves and each other to form still longer chain materials. Of course, the longer the carbon chain, the more susceptible the compound is to being cracked. Therefore, where successive oligomerization zones are used, the oligomerization zones must be operated under conditions which will not cause the oligomers to crack or engage in hydrogen transfer reactions. The most convenient, and preferred, method of operation where multiple reaction zones are used, is to operate each zone under reaction conditions less severe than the preceding oligomerization zone. Operating with oligomerization zones in series with decreasing severity makes process control of the exothermic oligomerization reactions much easier.

One particularly desirable method of operation is to separate unreacted alkenes present in the effluent of any reaction zone from the olefin oligomers present in the effluent of the particular zone and then to recycle the unreacted alkenes back into the feed.

The run life of the catalyst in the reaction zones can be greatly and surprisingly increased by periodically stopping the flow of feed into the reaction zone and stripping the catalyst with a stripping gas (such as hydrogen, nitrogen, or water vapor).

FIGURES

FIG. 1 illustrates hydrogen transfer index data for several different catalysts as well as the relation of the index to conversion.

FIG. 2 shows the relation between time onstream and production of 288° C. (550° F.)+product for the two-step process as opposed to a one-step process for preparing high boiling hydrocarbons from propene.

EXAMPLE 1

A series of experiments was performed to examine the hydrogen transfer activity of molecular sieves. A feed pulse of fixed volume (0.5 microliter) from a heated Valco valve was carried into a small, fixed catalyst bed located in a stainless steel reactor. The reaction was entirely gas phase and isothermal. The hydrocarbon feed pulse was carried to the catalyst bed by a known velocity nitrogen stream at a high linear rate. The nitrogen stream was passed through a 4A/5A molecular sieve purifier before contacting the feed. The catalyst bed contained −250 mesh catalyst fines which, depending on the catalyst, were diluted with the same size mesh alumina. The diluent alumina was added as needed to reduce the catalyst activity so all catalysts could be measured at roughly identical feed conversions. The catalyst was finally diluted (4:1) with 80–100 mesh, acid washed Alundum to improve catalyst dispersion and to help maintain a true isothermal bed temperature. Reactor pressure was controlled by an Annin valve.

The entire gas stream, containing the reacted feed pulse, was taken directly through heated lines to the injector splitter of a capillary gas chromatograph equipped with a flame ionization detector.

The reaction conditions include a catalyst temperature of 221° C. (430° F.), total pressure of 34.5 bar (500 psi) and a nitrogen carrier gas flow of 800 cc/min. at STP. The injection volume was 0.5 microliter. Hydrocarbon analysis was performed using a 50-meter OV-101 fused silica capillary column. The catalyst was continually exposed to the nitrogen carrier gas between injections.

The hydrogen transfer index calculated from the test results is the ratio of 3-methylpentenes to 3-methylpentane produced from a 1-hexene feed, with a linear hexene conversion from 30% to 70%.

The contact time was computed from the temperatures and pressure corrected linear velocity of the nitrogen carrier stream and the length and volume of the catalyst bed. The computed WHSV and catalyst/oil ratio were based solely on the active component content within the bed.

The catalysts tested are listed in Table 1.

TABLE 1

| Catalyst | $SiO_2/Al_2O_3$ Mole Ratio |
|---|---|
| (A) ZSM-5 | 78:1 |
| (B) Silicalite | 230:1 |
| (C) Silicalite | 2200:1 |
| (D) Ultrastable Y | 6:1 |
| (E) Dealuminated Mordenite | 63:1 |
| (F) Amorphous $SiO_2/Al_2O_3$ | 54/46 (wt. ratio) |
| (G) CZH-5 | 50:1 |

The results obtained are listed in Table 2. Experiments with Catalysts (A) and (B) were performed after impregnating the catalysts with 0.8 weight percent zinc.

TABLE 2

| Catalyst | 20% A 80% $Al_2O_3$ | 20% A 80% $Al_2O_3$ | 65% B | 65% C | 12% D 88% $Al_2O_3$ | 18% E 82% $Al_2O_3$ | 100% F | 100% G |
|---|---|---|---|---|---|---|---|---|
| Inj. Number | 3 | 3 | 3 | 2 | 3 | 1 | 2 | 1 |
| Catalyst Wt (mg Sieve) | 4.4 | 4.1 | 19 | 24 | 2.8 | 4.2 | 35 | 19.3 |
| Zn (0.8%):Yes/No | No | Yes | Yes | No | No | No | No | No |
| Alundum Dilution | 4:1 | 4:1 | 4:1 | 3:1 | 4:1 | 4:1 | 4:1 | 4:1 |
| Contact Time (sec) | 0.25 | 0.36 | 0.33 | 0.41 | 0.28 | 0.23 | 0.34 | 0.4 |
| WHSV (1/hr) | 1100 | 806 | 200 | 120 | 1500 | 1220 | 100 | 157 |
| Cat/Oil | 13 | 12 | 57 | 71 | 9 | 13 | 104 | 57 |
| Conversion From Linear Hexenes (%) | 47 | 42 | 41 | 56 | 38 | 48 | 43 | 53 |
| $K_{Hexenes}$ (1/sec) | 2.54 | 1.51 | 1.60 | 2.00 | 1.71 | 2.84 | 1.65 | 1.88 |
| Product Yield, Wt % | | | | | | | | |
| $C_4$ Minus | 13 | 12.6 | 14 | 13.3 | 3.5 | 17.1 | 0.3 | 12 |
| $C_5$ | 11 | 10 | 8.4 | 8.5 | 4.2 | 12.9 | 3 | 8 |
| $C_6$ | 57 | 58.8 | 62 | 53.6 | 63.2 | 55.7 | 76.4 | 73 |
| $C_7$ | 4 | 4.2 | 4.1 | 5.5 | 4.7 | 4.4 | 3.5 | 2 |
| $C_8$ | 7.5 | 5.6 | 5.4 | 7.9 | 5.9 | 5.2 | 4.1 | 3.7 |
| $C_9$ | 4 | 3.6 | 2.5 | 4.3 | 4.3 | 2.4 | 2.4 | 1.3 |
| $C_{10}^+$ | 1.9 | 2.8 | 2.3 | 4.9 | 10.7 | 1.1 | 10.1 | 0.3 |
| Hydrogen Transfer Index | | | | | | | | |
| 3M-Pentenes/ | 66 | 70 | 105 | 500 | 0.30 | 1.0 | .5 | 6 |

TABLE 2-continued

| Catalyst | 20% A 80% Al₂O₃ | 20% A 80% Al₂O₃ | 65% B | 65% C | 12% D 88% Al₂O₃ | 18% E 82% Al₂O₃ | 100% F | 100% G |
|---|---|---|---|---|---|---|---|---|
| 3M-Pentane | | | | | | | | |

The graph of FIG. 1 illustrates the differences in hydrogen transfer index for several catalysts, as well as the response of the hydrogen transfer index to the number of hexene injections, i.e., to the fouling of the catalyst.

A high hydrogen transfer index is characteristic of a catalyst with low hydrogen transfer activity. The hydrogen transfer index should be above 10, preferably above 25.

EXAMPLE 2

Propene was polymerized over a zinc (1 wt. %) silicalite catalyst in two steps. Reaction conditions were as follows:

| | First Stage | Second Stage |
|---|---|---|
| Pressure | atmospheric | 55 bar (800 psig) |
| Temperature | 288° C. (550° F.) | 288° C. (550° F.) |
| LHSV | 2 | 0.5 |

The $C_5+$ yield from the first stage was 70–80 wt. %, of which 92% was alkene. The product produced had the characteristics shown below as compared with a one-step propene oligomerization performed at LHSV of 0.5, 288° C. (550° F.), and 110 bar (1600 psig):

| Product Yields, Wt. % | Two Step Process | One-Step Process |
|---|---|---|
| $C_3$–$C_4$ paraffins | 1.8 | 6.8 |
| $C_3$–$C_4$ olefins | 19.0 | 0 |
| $C_5$–93° C. (200° F.) | 9.3 | 14.5 |
| 93° C.–177° C. (350° F.) | 19.6 | 24.6 |
| 177° C.–232° C. (450° F.) | 23.2 | 22.2 |
| 232° C.–288° C. (550° F.) | 15.6 | 15.6 |
| 288° C.+ | 11.5 | 16.3 |

With the $C_3$–$C_4$ olefins recycled from the first stage effluent into the first stage feed, the two-stage process becomes a highly efficient method of producing high boiling materials.

A run life test comparing the two-step and one-step processes described above was performed. The second stage catalyst was rejuvenated twice by stripping with hydrogen at 427° C. (800° F.) and 13.8 bar (200 psig). FIG. 2 shows the relationship between 288° C. (550° F.)+production and time onstream. The data show the desirability of a two-stage as opposed to a one-stage process.

EXAMPLE 3

A propene/propane 3/1, w/w mixture was contacted with a silicalite/alumina (65/35, w/w) catalyst at 316° C. (600° F.), LHSV of 2, 0 $H_2$/HC, and atmospheric pressure to illustrate a typical first-stage product which would be fed to the second, high-boiling hydrocarbon producing step.

| Yields | Wt. % |
|---|---|
| $C_1$–$C_2$ | 0.1 |
| propene | 3 |
| propane | 23 |
| $C_4$ alkenes | 12 |
| $C_4$ alkanes | 2 |
| $C_5$–93° C. (200° F.) | 34 |
| 93° C.–182° C. (360° F.) | 26 |
| (Total $C_5+$ -60%) | |

When the $C_5+$ fraction is fed to the second, pressurized step, very high-boiling range hydrocarbons are produced.

I claim:

1. A process for preparing high boiling hydrocarbons from normally gaseous olefins, comprising:
   (a) contacting a feed comprising normally gaseous olefins with a first catalyst comprising an intermediate pore size silicaceous crystalline molecular sieve substantially free of hydrogen transfer activity selected from silicalite, an organosilicate disclosed in RE 29,948 and CZM, to produce a first effluent comprising normally liquid olefins; and
   (b) contacting at least part of the normally liquid olefins contained in said first effluent with a second catalyst comprising an intermediate pore size silicaceous crystalline molecular sieve substantially free of hydrogen transfer activity under oligomerization conditions to produce a second effluent wherein said second effluent comprises oligomers of said normally liquid olefins and wherein at least some of said oligomers are liquids under said oligomerization conditions.

2. The process of claim 1, further comprising the step of hydrogenating at least part of said second effluent.

3. The process of claim 1, further comprising:
separating unreacted normally gaseous olefins from said first effluent; and
recycling the olefins so separated back into the feed of step (a).

4. The process of claim 1, further comprising:
separating unreacted normally liquid olefins from said second effluent; and
recycling the olefins so separated back into the feed for step (b).

5. The process of claim 1 wherein said contacting of step (a) is performed at substantially atmospheric pressure.

6. The process of claim 1, 2, 3, 4, or 5 wherein the pressure in said second zone is greater than about 30 bar.

7. The process of claim 6 wherein the pressure in said second zone is greater than about 60 bar.

8. The process of claim 1, 2, 3, 4, or 5 wherein the temperature in said second zone is less than about 350° C.

9. The process of claim 1, 2, 3, 4, or 5 wherein said catalyst further comprises nickel or a compound thereof, zinc or a compound thereof, cadmium or a compound thereof, or mixtures thereof.

10. The process of claim 1, 2, 3, 4, or 5, further comprising the steps of: periodically stopping the contacting with the catalyst of step (a), step (b), or both, stripping said catalyst with a stripping gas, and resuming said contacting.

* * * * *

UNITED STATES PATENT AND TRADEMARK OFFICE
CERTIFICATE OF CORRECTION

PATENT NO. : 4,414,423
DATED : November 8, 1983
INVENTOR(S) : STEPHEN J. MILLER

It is certified that error appears in the above-identified patent and that said Letters Patent are hereby corrected as shown below:

Col. 3, line 26, "crystalling" should read --crystalline--.

Col. 4, line 56, "4,129,424" should read --4,229,424--.

Signed and Sealed this

First Day of May 1984

[SEAL]

*Attest:*

GERALD J. MOSSINGHOFF

*Attesting Officer*   *Commissioner of Patents and Trademarks*